United States Patent
Horinouchi et al.

(10) Patent No.: US 11,702,721 B2
(45) Date of Patent: Jul. 18, 2023

(54) MEDICAL PT ALLOY WIRE AND MEDICAL PT ALLOY COIL

(71) Applicant: TANAKA KIKINZOKU KOGYO K.K., Tokyo (JP)

(72) Inventors: Yuki Horinouchi, Isehara (JP); Michimasa Okubo, Isehara (JP); Mizuki Nihei, Isehara (JP); Akira Inoue, Isehara (JP); Takeyuki Sagae, Isehara (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 0 days.

(21) Appl. No.: 17/940,957

(22) Filed: Sep. 8, 2022

(65) Prior Publication Data

US 2023/0084270 A1     Mar. 16, 2023

(30) Foreign Application Priority Data

Sep. 13, 2021   (JP) ................... 2021-148526

(51) Int. Cl.
*C22C 5/04* (2006.01)
(52) U.S. Cl.
CPC ..................................... *C22C 5/04* (2013.01)
(58) Field of Classification Search
CPC ..................................... C22C 5/04; C22F 1/14
See application file for complete search history.

(56) References Cited

U.S. PATENT DOCUMENTS

| | | |
|---|---|---|
| 2006/0197542 A1 | 9/2006 | Tanaka |
| 2021/0069386 A1 | 3/2021 | Chen et al. |
| 2021/0069387 A1 | 3/2021 | Chen et al. |

FOREIGN PATENT DOCUMENTS

| | | |
|---|---|---|
| CN | 109385591 A | 2/2019 |
| JP | 2005-233967 A | 9/2005 |
| JP | 2006-129935 A | 5/2006 |
| JP | 2016-130351 A | 7/2016 |

OTHER PUBLICATIONS

Extended European Search Report issued in connection with EP Appl. Ser. No. 22184677.7 dated Dec. 12, 2022 (9 pages).

*Primary Examiner* — Jessee R Roe
(74) *Attorney, Agent, or Firm* — Foley & Lardner LLP

(57) ABSTRACT

The present invention is drawn to a medical Pt alloy wire, made of a Pt—W alloy containing 10% by mass or more and 15% by mass or less of W, a balance of Pt, and inevitable impurities. The Pt alloy wire has Vickers hardness of 400 Hv or more and 600 Hv or less, and has hardness and strength superior to those of a conventional Pt alloy wire having the same composition. The Pt alloy wire of the present invention has properties preferable as a coil applied to an embolic coil or a guide wire or the like, and is also good in workability in secondary processing for producing such a medical tool.

5 Claims, 2 Drawing Sheets

Pt-12%W (No. 3: PROCESS ANNEALING PERFORMED

Pt-12%W (No. 5: PROCESS
ANNEALING NOT PERFORMED

Pt-16%W (No. 9: PROCESS
ANNEALING PERFORMED

MEDICAL PT ALLOY WIRE AND MEDICAL PT ALLOY COIL

CROSS-REFERENCE TO RELATED APPLICATIONS

This application claims priority to Japanese Application No. 2021-148526, filed on Sep. 13, 2021. The content of this application is hereby incorporated by reference in its entirety.

BACKGROUND OF THE INVENTION

Field of the Invention

The present invention relates to a medical Pt alloy wire suitably used as a material of medical tools such as an embolic coil and a guide wire. More particularly, it relates to a Pt alloy wire that is more excellent in mechanical properties than a conventional medical Pt alloy wire, and is also good in workability in secondary processing such as coiling processing.

Description of the Related Art

An embolic coil used in a treatment of a cerebrovascular disease, such as subarachnoid hemorrhage, for preventing rupture of a cerebral aneurysm, or a guide wire used for guiding a catheter in a catheter treatment is produced by forming an extra fine metal wire into a coil shape by coiling processing.

A medical tool such as an embolic coil is a tool brought into direct contact with a human body, and sometimes embedded in a human body. Therefore, a constituent material of the tool is required to have chemical stability and biocompatibility. Besides, in consideration of use conditions of an embolic coil retained within a pulsating/beating blood vessel, and a guide wire repeatedly deformed and moved within a bending blood vessel, the material is required to have mechanical properties such as strength and a spring property. In addition, in a treatment using such a medical tool, the position of the tool is usually checked by X-ray photography, and hence a metal material having X-ray visibility is suitably used. As the constituent material of such a medical metal wire, various metal materials such as Pt alloy, Ti alloy and stainless steel are employed.

Among these metal materials, use of alloy wires principally containing Pt, that is, a precious metal, is particularly expected in recent years. Pt is a metal particularly excellent in biocompatibility, and in addition, has a high atomic weight and is good in X-ray visibility. For example, Patent Document 1 discloses a guide wire of a Pt alloy wire containing a Pt—W alloy. According to the disclosure of this Patent Document 1, a Pt alloy wire containing a Pt—W alloy having a W concentration of 3% by mass or more and 15% by mass or less is applied. It is also disclosed that an alloy wire having a W concentration of 8% by mass has the maximum strength, and exhibits tensile strength of 1850 MPa (N/mm$^2$).

PRIOR ART DOCUMENT

Patent Document

Patent Document 1: Japanese Patent Application Laid-Open No. 2006-129935

SUMMARY OF THE INVENTION

Technical Problem

Since a medial tool such as a guide wire or an embolic coil is used on a human body, behavior disorder, accidental damage, and breakage should be avoided during use as much as possible. Therefore, a metal wire to be used in a medical tool is required to be further improved in more suitable mechanical properties.

Besides, the medical tool such as an embolic coil or a guide wire is produced by subjecting a metal wire to secondary processing such as coiling processing or weaving/Flemish weaving processing. In the secondary processing, a poor finish as a product such as a surface defect should be avoided. Therefore, regarding the metal wire for a medical tool, consideration should be paid to an assurance of workability in such secondary processing and suppression of strength degradation through the processing.

Accordingly, an object of the present invention is to provide a metal wire for a medical tool in the shape of a coil or the like that has mechanical properties more suitable than conventional ones, and has biocompatibility, X-ray visibility and the like. In addition, in consideration of processing into a coil or the like, the present invention provides a medical metal wire also having good properties of workability.

Solution to Problem

The present inventors selected, as a basic composition of an alloy wire, a Pt—W alloy as in Patent Document 1. This is because, as described above, Pt possesses biocompatibility and the like regarded significant as a medical material. In addition, W is applied as an additional element because W is also a metal having a high atomic weight, and hence X-ray visibility is ensured. Besides, in consideration of medical use of the present invention, it is not preferable means to employ a novel additional element. A metal wire obtained by employing a novel additional element may be improved in physical properties such as strength, but it is not clear whether or not the metal wire possesses safety/stability as a medical material. Since a medical material is used on a human body, its safety evaluation is not easy. In this respect, a Pt—W alloy has produced results as a constituent material of a medical alloy wire, and its safety/stability is ensured.

Here, regarding the mechanical properties of the Pt—W alloy wire, as disclosed in Patent Document 1, in a range of a W concentration of 3% by mass or more and 15% by mass or less, the maximum tensile strength (1850 MPa) is exhibited when the W concentration is about 8% by mass. It is described that the strength tends to be lowered when the W concentration exceeds 8% by mass.

The present inventors thought that a factor of this behavior of the conventional Pt—W alloy wire is that a difference is caused in working process of the wire depending on change in workability of the Pt—W alloy caused by the W concentration increase. A metal wire is usually produced from an alloy ingot through combination of hot working and cold working (wire drawing). The cold working has effects of not only shape adjustment (wire diameter adjustment) of a material to be worked but also improving strength through work strengthening (dislocation hardening) and adjustment of material structure. On the other hand, in a Pt—W alloy, W is originally an additional element for increasing the strength of the resultant alloy. Although the increase of the content of W increases the strength of the alloy itself, however, the increase tends to make the cold working difficult. Therefore, in order to produce a wire from an alloy having an increased W concentration without causing disconnection and crack, the man-hour or processing rate of the cold working is unavoidably reduced. The strength of a conventional Pt—W alloy wire is lowered when the W concentration exceeds 8% by mass probably because the cold working is difficult to perform due to strength increase of the alloy and hence strengthening by the cold working is insufficient.

If this consideration is proper, a wire having original mechanical properties of a Pt—W alloy can be obtained by optimizing production process (working process) of a Pt—W alloy wire. Therefore, the present inventors examined, with optimizing the production process of a Pt—W alloy wire, relation between a composition range (W concentration range) through the optimization and mechanical properties. As a result, the following findings were obtained:

(1) A Pt—W alloy wire of the present inventors can exhibit strength higher than that of a conventional one, and even a Pt—W alloy wire having a W concentration of 8% by mass can exhibit tensile strength of 2000 MPa or more.

(2) Even in a Pt—W alloy wire having a W concentration of 8% by mass or more, a trend toward increase of tensile strength owing to W concentration increase can be caused.

(3) In a Pt—W alloy wire, there is a correlation between hardness and tensile strength.

(4) A Pt—W alloy wire having excessively high hardness/tensile strength, however, can affect workability in secondary processing for forming the wire into a coil or the like.

As a result of earnest studies made based on the findings (1) to (4), the present inventors conceived the present invention as a Pt—W alloy medical wire specified by preferable composition range and hardness.

Specifically, the present invention is drawn to a medical Pt alloy wire including a Pt—W alloy containing 10% by mass or more and 15% by mass or less of W, a balance of Pt, and inevitable impurities, and having Vickers hardness of 400 Hv or more and 600 Hv or less. Now, the Pt—W alloy wire of the present invention will be described in detail.

(I) Structure of Medical Pt Alloy Wire of Invention (A) Composition of Pt Alloy

The Pt alloy wire of the present invention contains the Pt—W alloy having a W concentration of 10% by mass or more and 15% by mass or less. As described above, in the Pt alloy wire of the present invention, there is a proportional relationship between the W concentration and the hardness or tensile strength, and increase of the W concentration increases the hardness. An alloy wire having a W concentration exceeding 15% by mass has, however, high hardness/strength but this high W concentration can affect workability in processing the wire into a coil or the like. The workability embraces not only whether the processing can be performed against increase of processing resistance but also a processing quality such as a crack obtained after the processing. On the other hand, when the W concentration is less than 10% by mass, the hardness is low. The wire of the present invention exhibits higher tensile strength and hardness than the conventional one (Patent Document 1) even when the W concentration is 8% by mass, but the lower limit of the W concentration is 10% by mass for obtaining a more preferable Pt alloy wire.

It is noted that a preferable W concentration of the present invention is 10% by mass or more and 14% by mass or less. For obtaining a wire with more preferable workability, the upper limit of the W concentration is thus further restricted.

Although there is no need to especially limit a method for measuring the W concentration in a Pt—W alloy wire, inductively coupled plasma emission spectral analysis (ICP emission spectral analysis), X-ray fluorescence analysis (XRF analysis) or the like can be applied. In the ICP emission spectral analysis, a Pt—W alloy wire is cut into small pieces if necessary, and liquefied with hydrofluoric acid, and the resultant solution is analyzed with an ICP emission spectral analyzer. In the XRF analysis, a Pt—W alloy wire is embedded in a conductive resin, and a cross section of the resultant resin is polished to be analyzed with an XRF analyzer. Besides, a principal component of a Pt—W alloy can be easily measured not only by these analysis methods but also by another analysis method such as an energy dispersive X-ray analysis (EDX) or wavelength dispersive X-ray analysis (WDX).

The Pt—W alloy of the Pt alloy wire of the present invention substantially contains Pt and W, and a balance excluding W corresponds to Pt. Inevitable impurities can be, however, contained. As the inevitable impurities, Zr (zirconium), Ca (calcium), Al (aluminum), Si (silicon), Ir (iridium), Pd (palladium), Rh (rhodium) and the like may be contained. A total content of such impurities is preferably 0.5% by mass or less, and more preferably 0.2% by mass or less. Besides, it is Zr and Ca that are impurity elements to be particularly regulated. These two impurity elements may affect the workability of the Pt—W alloy, and the influence is caused at the stage of processing from an ingot to a wire. Therefore, it is preferable that a Zr content is 1000 ppm or less, and a Ca content is 250 ppm or less in the Pt—W alloy. For measuring the contents of these inevitable impurities, not only the ICP analysis and the XRF analysis described above but also a known analysis method such as glow discharge mass spectrometry (GD-MS analysis) can be applied.

(B) Mechanical Properties of Pt Alloy Wire of Invention (B-1) Vickers Hardness

The Pt alloy wire of the present invention is characterized by the above-described W concentration (of 8% by mass or more and 15% by mass or less), and Vickers hardness. In the present invention, high hardness and tensile strength that cannot be exhibited by a conventional Pt—W alloy wire can be attained. This is owing to structural change caused in a material through working process of a wire described below. It is presumed that the structural change in a material is caused by complex actions of a plurality of structural factors including optimization of a material structure as well as the density and the state of dislocation introduced during a cold working step, and existence state of the W element added in the above-described range. These structural factors are not all cleared, and hence the W concentration and the hardness are used to specify the structure of the Pt alloy wire in the present invention.

The Vickers hardness of the Pt alloy wire of the present invention is 400 Hv or more and 600 Hv or less. A wire having Vickers hardness of less than 400 Hv has strength equivalent to or slightly higher than that of a conventional Pt alloy wire, and hence it is not significant to distinguish from such a wire. On the other hand, when Vickers hardness exceeds 600 Hv, workability in secondary processing of the wire into a coil or the like is not good. The hardness of the wire is preferably 400 Hv or more and 550 Hv or less.

It is noted that the Vickers hardness of an alloy wire can be measured generally with a Vickers hardness tester or a micro Vickers hardness tester under known conditions. For example, a method according to JIS Z 2244 "Vickers hardness test—Test method" can be employed for the measurement.

(B-2) Tensile Strength

In the Pt alloy wire of the present invention, there is a correlation between the Vickers hardness and tensile strength (UTS). The Pt alloy wire of the present invention has tensile strength (UTS) of 2500 MPa or more. An upper limit of the tensile strength of the Pt alloy wire is 3500 MPa or less. This is because a wire having excessively high tensile strength is in a state not preferable in workability. The tensile strength of the Pt alloy wire is more preferably 2500 MPa or more and 3300 MPa or less, and further preferably 2500 MPa or more and 3200 MPa or less. It is noted that such values of the tensile strength are in a range higher than that described in the conventional technique (Patent Document 1).

For measuring the tensile strength of a Pt alloy wire, a usual tensile test for a metal wire (such as a tensile test according to JIS Z 2241 "Metallic materials —Tensile testing—Method of test at room temperature") can be employed for the measurement.

(B-3) Other Properties (B-3-1) Reduction of Area

In the Pt alloy wire of the present invention, reduction of area in the tensile test is preferably 35% or more. The reduction of area has relation to the workability in the secondary processing of forming the wire into a coil or the like. When the reduction of area of the Pt alloy wire is 35% or more, the wire can be processed into a coil with occurrence of disconnection and crack suppressed. The reduction of area is more preferably 50% or more. An upper limit of the reduction of area is preferably 70%. For measuring the reduction of area, a cross sectional area $W_0$ of a wire before the tensile test and a cross sectional area $W$ of the wire after the tensile test (after fracture) are measured in the tensile test, and the reduction of area is calculated in accordance with an expression $(W_0-W)/W_0 \times 100$.

(B-3-2) Young's Modulus

The Pt alloy wire of the present invention has characteristic mechanical properties as compared with a conventional Pt alloy wire having the same composition. As properties in addition to those described above, the Pt alloy wire of the present invention preferably has a Young's modulus of 230 GPa or more and 290 GPa or less.

(C) Material Structure of Pt Alloy Wire

The Pt alloy wire of the present invention has a material structure in which laterally long crystal grains are collected in a lengthwise direction in an arbitrary cross section in the lengthwise direction. The crystal grains contained in the material structure have an aspect ratio (major axis length/minor axis length) of 30 or more on average. Besides, in this material structure, needle crystals having a larger aspect ratio than those present therearound because of elongation in the isometric direction through wire drawing are dispersed. It is difficult to measure the aspect ratio of the needle crystals, and the minor axis length is 1/30 or less of the wire diameter of the Pt alloy wire. It is presumed that such a material structure is formed based on production process described below, and is regarded as one of factors that the Pt alloy wire of the present invention exhibits high hardness and tensile strength.

(D) Wire Diameter of Pt Alloy Wire

In the Pt alloy wire of the present invention, the wire diameter is preferably 20 μm or more and 100 μm or less. In the medical use as an embolic coil, a guide wire and the like, a metal wire having a wire diameter falling in this range is used in many cases.

(II) Method for Producing Medical Pt Alloy Wire of Invention

In production of the Pt alloy wire of the present invention, a usual method for producing a wire is basically employed. Here, in the usual method for producing a wire, an alloy ingot is subjected to hot working such as hot forging for dimensional adjustment with a cast structure of the alloy ingot broken, and then the resultant is subjected to cold working such as cold wire drawing, and thus, a wire having a desired wire diameter can be obtained.

The Pt alloy wire of the present invention is provided with high hardness/high tensile strength and workability with the W concentration set at 10% by mass or more and 15% by mass or less. As improvement of the working process for obtaining such properties, plastic strain accumulated before forming the wire from the alloy ingot is optimized in the present invention. In consideration of a step of introducing the optimized plastic strain, contents of respective steps of the method for producing a Pt alloy wire of the present invention will now be described.

(a) Preparation of Pt—W Alloy Ingot

First, a Pt—W alloy ingot having a W concentration of 10% by mass or more and 15% by mass or less is prepared. The Pt—W alloy ingot can be produced by mixing Pt and W into a desired composition, and casting the resultant mixture by arc melting or vacuum melting. In order to control the shape for hot working to be performed in the next step, the casted alloy may be melted again to obtain an alloy ingot. The shape of the alloy ingot to be prepared for the hot working step is a rod shape, a plate shape or the like, and is not especially limited.

(b) Hot Working Step

The hot working step is an essential step for breaking the cast structure of the alloy ingot. Besides, the cross sectional area of the alloy ingot is reduced through the hot working step to obtain a crude wire suitable for cold working. In the hot working step, hot swaging, hot casting, and hot rolling (hot groove rolling) are performed. Such hot working procedures may be combined to perform the hot working a plurality of times. A processing temperature employed in the hot working step is preferably 600° C. or more and 1100° C. or less.

In the hot working step of the present invention, the hot working is performed preferably for obtaining a cross section reduction rate of 45% or more through the working. This is for making the material structure more homogeneous in addition to the breakage of the cast structure. Thus, workability in cold working to be performed in the next step can be improved. The cross section reduction rate is calculated based on a cross sectional area ($S_0$) of the alloy ingot before the hot working and a cross sectional area (S) of the crude wire obtained after the hot working (after the last hot working procedure if the hot working is performed a plurality of times) $((S_0-S)/S_0 \times 100)$.

(d) Cold Working Step

Through the cold working step, a Pt alloy wire having a desired wire diameter is produced. In the cold working step, cold rolling (cold groove rolling), cold wire drawing, cold drawing and the like are performed. Such cold working procedures may be combined to perform the cold working a plurality of times. A processing temperature employed in the cold working step is preferably ordinary temperature or more and 200° C. or less.

(e) Setting of Equivalent Strain (Process Annealing Treatment)

As described so far, the Pt alloy wire of the present invention is excellent in workability (workability in secondary processing) in spite of its high strength. In the production of the Pt alloy wire, it is preferable to control the W concentration as well as to control an equivalent strain (accumulated plastic strain) in the production procedures described above. Here, the equivalent strain herein refers to a plastic strain amount accumulated, with an alloy having no plastic strain regarded as a reference, until the alloy is processed into a wire through the processing procedures.

In the present invention, the alloy is processed into a wire through a processing method principally employing extruding/drawing processing with a die or a grooved roll, or dieless wire drawing processing (drawing processing). An equivalent strain caused in the extruding/drawing processing is approximate to an absolute value of $\ln(A/A_0)$, wherein a cross sectional area of an alloy having no plastic strain is $A_0$, and a cross sectional area of a wire obtained after the cold working step is A. Besides, an alloy having no plastic strain is an alloy from which strain has been removed by an annealing treatment, or a casted alloy ingot.

In the production of the Pt alloy wire of the present invention, the equivalent strain calculated by the above-described approximate expression is preferably set to 2.0 or more and 8.0 or less. When the equivalent strain is set to less than 2.0, the hardness/tensile strength of the Pt alloy wire is lowered to be equivalent to that of the conventional technique. On the other hand, when the processing is performed with the equivalent strain set to beyond 8.0, the workability of the Pt alloy wire is so low that disconnection or the like may occur in the secondary processing into a coil or the like. The equivalent strain is more preferably set to 6.0 or less.

Based on the significance of the equivalent strain, an annealing treatment for releasing a plastic strain is preferably appropriately performed for adjustment of the equivalent strain. As a condition for the annealing treatment, the Pt alloy is heated preferably at a temperature of 600° C. or more and 1100° C. or less. When the temperature is less than 600° C., the strain is insufficiently released. The annealing treatment has an effect of improving workability in the cold working when performed before the cold working, but when the temperature is less than 600° C., this effect of improving the workability is also insufficient. On the other hand, when the annealing treatment is performed at a temperature beyond 1100° C., the Pt alloy is conspicuously softened due to recrystallization.

The number of times of performing the annealing treatment is not limited. The annealing treatment may be performed a plurality of times before the hot working step, during the hot working step, or after the hot working step (after the last procedure of the hot working), and before the cold working step or during the cold working step. Since the equivalent strain is based on the cross sectional area of the Pt alloy after the annealing treatment, however, the annealing treatment is preferably performed in consideration of the number of man-hours after the annealing treatment and the processing rate. The number of man-hours and the processing rate can be appropriately set based on the dimension of the Pt alloy and a target wire diameter of the Pt alloy wire.

An optimum target of the annealing treatment is, however, a Pt alloy after the hot working step (after the last procedure of the hot working) and before or during the cold working step. The annealing treatment performed at such timing is significant from the viewpoint of the adjustment of the equivalent strain. In consideration of the number of man-hours and the processing rate assumed in the cold working step, the annealing treatment should be performed after the hot working step for setting the equivalent strain in the preferable range. Alternatively, when the annealing treatment is performed before cold working, or during the cold working step, the workability in the cold working can be assured, and the alloy can be easily processed into a fine wire. In the present invention, this annealing treatment to be performed on a Pt alloy in a state after the hot working step and before completing the cold working step is sometimes referred to particularly as process annealing. According to examination made by the present inventors, even if annealing is not performed before or during the cold working, the processing into a wire itself can be performed, and a wire with a diameter of about 100 μm or less can be thus produced. Heating conditions in the process annealing are the same as those described above.

Through the respective steps described so far, the Pt alloy wire of the present invention is produced. As described above, in the Pt alloy wire of the present invention, the equivalent strain until the processing into a wire is made suitable, and processing conditions in the respective processing steps are restricted. As a result, a Pt—W alloy wire having a structure different from that of the conventional technique (Patent Document 1) can be produced.

(III) Pt Alloy Coil and Medical Tool of Invention

The Pt alloy wire of the present invention has suitable mechanical properties and is excellent in workability in the secondary processing, and hence is suitably used in a Pt alloy coil included in an embolic coil or a guide wire. A Pt alloy coil for a medical tool of the present invention can be obtained by coiling processing for winding the Pt alloy wire of the present invention.

A coil for a medical tool is a fine member for moving in a blood vessel of a human body produced by processing a Pt alloy wire having a minute wire diameter described above. Therefore, the coil for a medical tool is occasionally restricted in a coil index. A coil index is a ratio between a coil average diameter D and a wire diameter d (D/d), and in a coil for a medical tool, the coil index is set to about 4 to 5 in many cases. In consideration of the wire diameter of the wire, a processing rate of the coiling processing for such a coil index is high. The Pt alloy coil of the present invention is in a preferable state free from surface crack and the like even if subjected to such strong processing.

The Pt alloy coil can be used as a part or the whole of an embolic coil or a guide wire. An embolic coil is generally in a secondary coil shape. A secondary coil shape is formed by subjecting the Pt alloy coil of the present invention further to coiling processing. A guide wire (spring wire) is produced by winding the Pt alloy wire of the present invention around a core material (core) of an appropriate material. Both the embolic coil and the guide wire of the present invention can stably function without being easily broken owing to the preferable mechanical properties of the Pt alloy wire.

It is noted that the Pt alloy wire of the present invention can be used as a medical tool such as a stent, or a marker in addition to the embolic coil and the guide wire.

Advantageous Effects of Invention

As described so far, a medical Pt alloy wire of the present invention has mechanical properties and workability more preferable than those of a conventional Pt—W alloy wire. Thus, the medical Pt alloy wire of the present invention exhibits preferable properties as a constituent material of an embolic coil and a guide wire.

DETAILED DESCRIPTION OF THE PREFERRED EMBODIMENTS

Figure 1:
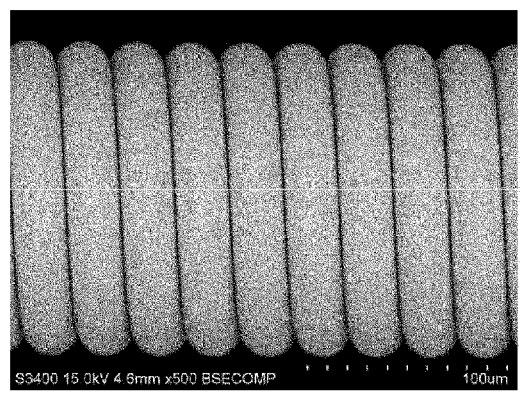
FIG. 1 shows photographs of a disconnection state obtained through coiling processing of Pt alloy wires having a W concentration of 12% by mass (with process annealing performed/not performed) and a W concentration of 16% by mass (with process annealing performed)
Figure 1:
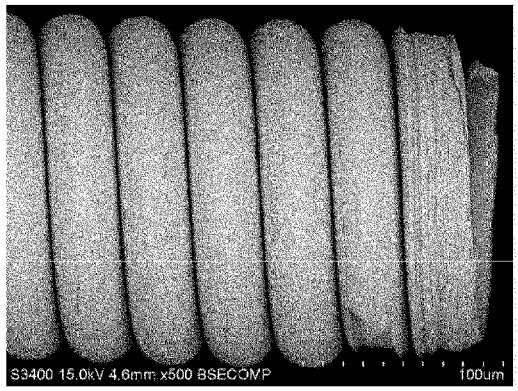
Figure 1:
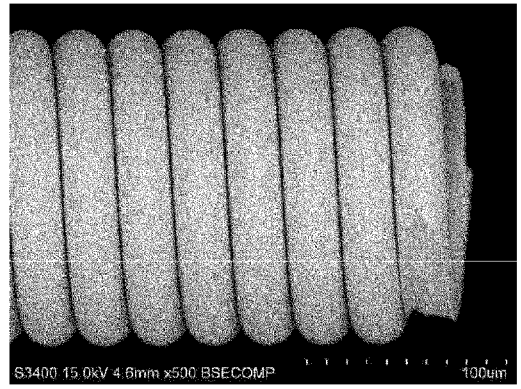

A preferred embodiment of the present invention will now be described. In the present embodiment, Pt—W alloy wires having different W concentrations were produced to measure their mechanical properties and evaluate their workability.

[Production of Pt Alloy Wires]

First, Pt metal (purity of 99.98%) and W (purity of 99.9%) were weighed and mixed to obtain a prescribed composition, and the resultant mixture was subjected to arc melting to produce a mother alloy. The mother alloy was vacuum melted to produce a Pt—W alloy ingot in the shape of a round bar (with a diameter of 10 mm). In the present embodiment, Pt—W alloys respectively having W concentrations of 8% by mass, 10% by mass, 12% by mass, 13% by mass, 14% by mass, 15% by mass, and 16% by mass were produced to produce Pt alloy wires having respective compositions.

Next, the bar-shaped Pt alloy ingot was processed into a crude wire through a hot working step. In the hot working step, the bar-shaped Pt alloy ingot was heated at 700° C. for 10 minutes, and then appropriately subjected to hot swaging and hot groove rolling, and thus, a crude wire having a wire diameter of 3.5 to 7.4 mm was formed. In this hot working step, a total area reduction rate was set to 45% or more.

After the hot working step, the crude wire was subjected to cold groove rolling and cold wire drawing at room temperature, and thus processed into a diameter of 0.5 mm. Then, the resultant was subjected to a process annealing treatment by heating at 800° C. for 60 minutes in a nitrogen atmosphere to release a plastic strain.

After the process annealing treatment, the resultant crude wire was subjected to cold wire drawing at room temperature, and further subjected to continuous wire drawing, and thus, the crude wire was processed into a Pt alloy wire having a wire diameter of 28 As a result of the cold working performed after the process annealing, an equivalent strain of the alloy wire was 5.8 (No. 1 to No. 4, and No. 6 to No. 9). Thereafter, the resultant was washed, and cut into samples having a length suitable for various measurements and evaluation.

In the present embodiment, a sample (No. 5) of a Pt alloy wire produced from the Pt alloy having a W concentration of 12% by mass without performing the process annealing was also produced for comparison. Although this sample was not subjected to the process annealing of the present invention, a heat treatment (at 700° C. for 10 minutes) performed before the hot working corresponds to an annealing treatment. Therefore, the diameter (10 mm) of the bar-shaped alloy ingot at the time of this heat treatment corresponds to a reference in calculating an equivalent strain, and the equivalent strain is 10.4.

Production conditions for the Pt alloy wires produced in the present embodiment are listed together in Table 1.

TABLE 1

| | Alloy Composition | | Hot Working Step | | | | | Cold Working Step | | | |
|---|---|---|---|---|---|---|---|---|---|---|---|
| | | | Hot Swaging 1 | | Wire | Total Area | | | | | |
| No. | Pt | W | Pass Area Reduction Rate | Hot Groove Rolling | Diameter after Hot Working | Reduction Rate by Hot Working | Process Annealing | Cold Groove Rolling | Cold Wire Drawing | Wire Diameter | Equivalent Strain |
| 1 | 92 | 8 | 25%, 12% | — | 7.4 mm | 45% | 800° C. | 12% | 15%, 12%, 6% | 28 μm | 5.8 |
| 2 | 90 | 10 | | | | | | | | | |
| 3 | 88 | 12 | | | 6.3 mm | 60% | | | | | |
| 4 | | | | | 5.0 mm | 75% | | | | | |
| 5 | | | | | | | — | | | | 10.4 |
| 6 | 87 | 13 | | 12% | 3.5 mm | 88% | 800° C. | | | | 5.8 |
| 7 | 86 | 14 | | | | | | | | | |
| 8 | 85 | 15 | | | | | | | | | |
| 9 | 84 | 16 | | | | | | | | | |

* Heating is performed at 700°C for 10 minutes at the beginning of the hot working step.

[Measurement of Mechanical Properties]

Each of the alloy wires (having a wire diameter of 28 μm, and a sample length of 200 mm) produced as described above was measured for Vickers hardness. As a preparation for the measurement, the alloy wire was cut into a length of 15 mm or less, and the cut wires were bundled, and embedded in and fixed with a resin with the lengthwise direction set to be vertical to the bottom of the resin. The resultant resin was polished with waterproof abrasive paper and diamond slurry for exposing/polishing a measurement surface. The measurement was performed with a Vickers hardness measuring device (product name: HM-200, manufactured by Mitutoyo Corporation) under a load of 50 gf.

Besides, a tensile testing machine for extra fine wires (Strograph E3-S: Toyo Seiki Seisaku-sho, Ltd.) was used to perform a tensile test on each alloy wire. Test conditions were a gauge length of 100 mm, and a cross-head speed of 10 mm/min. By this tensile test, tensile strength (UTS) was measured.

Furthermore, a modulus of elasticity and a modulus of rigidity were measured by a free resonance method. As a tester, a free resonance type Young's modulus/rigidity measuring device (JE-RT, JG-RT: Nihon Techno-Plus Co., Ltd.) was used to perform the measurement at room temperature. Then, based on a resonance frequency thus measured, a modulus of elasticity and a modulus of rigidity were calculated.

[Evaluation of Workability]

Workability was evaluated by subjecting each wire sample to coiling processing, and determining whether or not the wire was disconnected during the processing. The coiling processing was performed with a coil index (D/d) set to 4 and by winding the wire sample around a core material (with a diameter of 0.1 mm). When an alloy wire with a length of 10 m could be processed to the last through the coiling processing, this sample was determined to have good workability (good). When a wire was disconnected during the processing, the processing was terminated at that point, and this sample was determined to have poor workability (poor). The measurement results (at room temperature) of the mechanical properties, and the evaluation results of the workability are shown in Table 2.

ing that the Pt alloy wires (Nos. 3 and 4) having the same W concentration and subjected to the process annealing to adjust an equivalent strain to 5.8 were good in workability, it is understood that the equivalent strain is preferably controlled to improve the mechanical properties and to ensure the workability.

Figure 2:
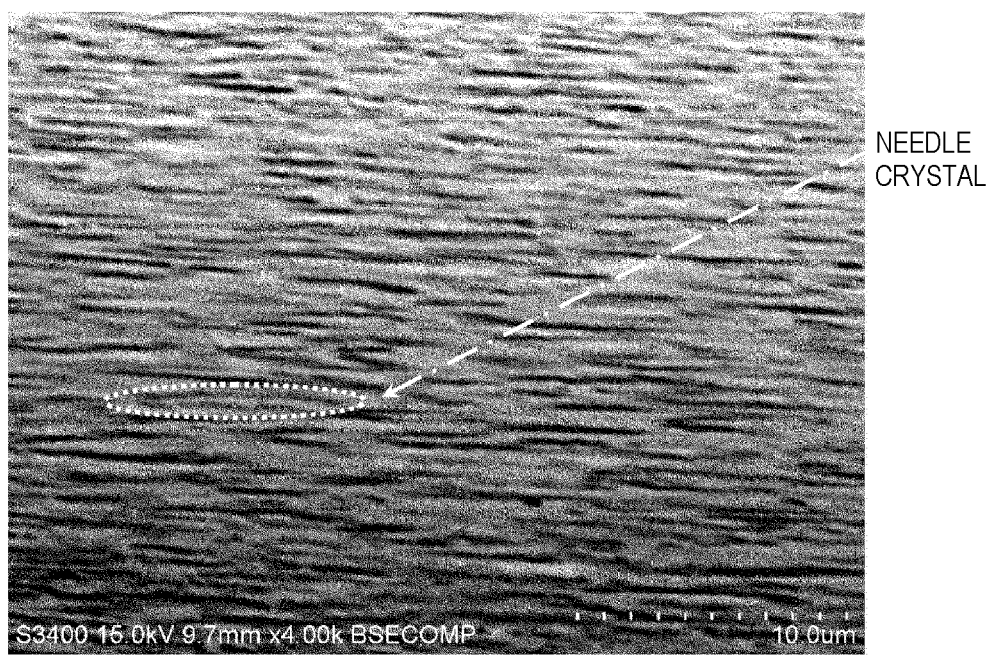
FIG. 2 shows an SEM photograph of a material structure, in a cross section in a lengthwise direction, of a Pt alloy wire having a W concentration of 12% by mass.

FIG. 2 shows an SEM photograph of a material structure, in a cross section in the lengthwise direction, of the Pt alloy wire (No. 4) having a W concentration of 12% by mass. As is understood from FIG. 2, the material structure of this Pt

TABLE 2

| | Alloy | | | | Mechanical Properties | | | | Evaluation |
|---|---|---|---|---|---|---|---|---|---|
| | Composition | | Process | Equivalent | Hardness | Tensile | Modulus of | Modulus of | of |
| No. | Pt | W | Annealing | Strain | (Hv) | Strength (Mpa) | Elasticity (Gpa) | Rigidity (Gpa) | Workability |
| 1 | 92 | 8 | 800° C. | 5.8 | 368 | 2450 | 228.3 | 86 | good |
| 2 | 90 | 10 | | | 455 | 2783 | 245.1 | 91.6 | good |
| 3 | 88 | 12 | | | 498 | 2996 | 259.1 | 96.6 | good |
| 4 | | | | | 485 | 2978 | 258.8 | 95.8 | good |
| 5 | | | — | 10.4 | 610 | 3056 | 260.1 | 96.8 | poor |
| 6 | 87 | 13 | 800° C. | 5.8 | 518 | 3025 | 262.7 | 98.4 | good |
| 7 | 86 | 14 | | | 536 | 3149 | 272.7 | 102.1 | good |
| 8 | 85 | 15 | | | 550 | 3159 | 269.8 | 101.5 | good |
| 9 | 84 | 16 | | | 605 | 3359 | 280.4 | 103.9 | poor |

Referring to Table 2, the Pt alloy wires having a W concentration falling in the range of the present invention (8% by mass or more and 15% by mass or less: No. 2 to No. 8) exhibit Vickers hardness of 400 Hv or more and tensile strength of 2500 MPa or more. Besides, it is understood that the hardness and the tensile strength of a Pt alloy wire increase in accordance with the increase of the W concentration. This is probably owing to strength increase of the Pt alloy by increase of the W concentration, and appropriate work strengthening by setting an equivalent strain in the cold working step.

The reduction of area was measured based on the tensile test results of the Pt alloy wires No. 2 to No. 8, and as a result, the wire No. 2 (having a W concentration of 10% by mass) had reduction of area of 65%, which was the maximum value, and the wire No. 8 (having a W concentration of 15% by mass) had reduction of area of 35%, which was the minimum value.

The Pt alloy wire (No. 9) having a W concentration of 16% by mass had hardness beyond 600 Hv. This Pt alloy wire was found to be poor in the workability because disconnection was caused through the secondary processing (coiling processing). Regarding the workability evaluation, FIG. 1 illustrates a disconnection state of coils obtained through the coiling processing of the Pt alloy wires having a W concentration of 12% by mass and a W concentration of 16% by mass. It is deemed, based on this result, that the hardness and the tensile strength of these Pt alloy wires are favorable, but the upper limit of the W concentration should be 15% by mass in consideration of the workability.

Alternatively, in the Pt alloy wire (No. 5) obtained from the wire having a W concentration of 12% by mass without performing the process annealing to adjust an equivalent strain to 10.4, the hardness was beyond 600 Hv, and disconnection was caused in the coiling processing. Consideralloy wire contained laterally long crystal grains having a high aspect ratio. A needle structure having a very small minor axis length got into this material structure. The aspect ratios of a plurality of crystal grains measured in FIG. 2 were all 30 or more.

Regarding the Pt alloy wire (No. 1) having a W concentration of 8% by mass, the tensile strength of a Pt alloy wire having the same composition described in Patent Document 1 of the conventional technique was 1850 MPa. Therefore, the Pt alloy wire of the present embodiment has strength higher than that obtained by the conventional technique even when the W concentration is 8% by mass. In the present invention, when strength increase by 50% or more as compared with that obtained by the conventional technique is set as a target value, the lower limit of the W concentration is suitably 10% by mass.

Industrial Applicability

A Pt alloy wire of a medical Pt—W alloy of the present invention has preferable mechanical properties and good workability. The present invention can be expected to be applied to a medical tool in the shape of a coil such as an embolic coil or a guide wire.

What is claimed is:

1. A medical Pt alloy wire, comprising a Pt—W alloy containing 10% by mass or more and 14% by mass or less of W, a balance of Pt, and inevitable impurities,
    wherein Vickers hardness of the medical Pt alloy wire is 400 Hv or more and 600 Hv or less; and a tensile strength of the medical Pt alloy wire is 2500 MPa or more and 3500 MPa or less.

2. The medical Pt alloy wire according to claim 1, wherein an average aspect ratio of crystal grains is 30 or more in a material structure of the wire in an arbitrary cross section in a lengthwise direction.

3. A Pt alloy coil for a medical tool, formed by winding of the medical Pt alloy wire defined in claim 1.

4. An embolic coil or a guide wire, comprising the Pt alloy coil for a medical tool defined in claim 3.

5. A Pt alloy coil for a medical tool, formed by winding of the medical Pt alloy wire defined in claim 2.

\* \* \* \* \*